(12) United States Patent
Dafni et al.

(10) Patent No.: US 8,571,172 B2
(45) Date of Patent: Oct. 29, 2013

(54) CT CONE BEAM SCANNER

(75) Inventors: Ehud Dafni, Caesarea (IL); Rafi Brada, Hod-HaSharon (IL); David Ruimi, Ganot Hadar (IL)

(73) Assignee: Arineta Ltd., Caesarea (IL)

( * ) Notice: Subject to any disclaimer, the term of this patent is extended or adjusted under 35 U.S.C. 154(b) by 474 days.

(21) Appl. No.: 12/937,290

(22) PCT Filed: Apr. 6, 2009

(86) PCT No.: PCT/IL2009/000385
§ 371 (c)(1),
(2), (4) Date: Oct. 11, 2010

(87) PCT Pub. No.: WO2009/128063
PCT Pub. Date: Oct. 22, 2009

(65) Prior Publication Data
US 2011/0033024 A1 Feb. 10, 2011

Related U.S. Application Data

(60) Provisional application No. 61/123,938, filed on Apr. 14, 2008.

(51) Int. Cl.
*A61B 6/03* (2006.01)
(52) U.S. Cl.
USPC .................................. 378/8; 378/11
(58) Field of Classification Search
USPC .......................... 378/4, 8, 9, 11, 15
See application file for complete search history.

(56) References Cited

U.S. PATENT DOCUMENTS

| 5,625,661 | A | 4/1997 | Oikawa | |
|---|---|---|---|---|
| 7,016,455 | B2 * | 3/2006 | Bruder et al. | 378/9 |
| 7,145,981 | B2 * | 12/2006 | Pelc | 378/9 |
| 7,444,011 | B2 * | 10/2008 | Pan et al. | 382/131 |
| 2004/0066880 | A1 | 4/2004 | Oikawa | |
| 2005/0238136 | A1 | 10/2005 | Bruder et al. | |
| 2006/0045234 | A1 * | 3/2006 | Pelc et al. | 378/9 |

FOREIGN PATENT DOCUMENTS

WO WO 2009/128063 10/2009

OTHER PUBLICATIONS

International Search Report Dated Aug. 4, 2009 From the International Searching Authority Re.: Application No. PCT/IL2009/000385.
Written Opinion Dated Aug. 4, 2009 From the International Searching Authority Re.: Application No. PCT/IL2009/000385.
Pack et al. "Investigation of Saddle Trajectories for Cardiac CT Imaging in Cone-Beam Geometry", Physics in Medicine and Biology, XP020023734, 49(11): 3217-2336, 2004. p. 2318-2322, Figs.1, 3, 4.
Wang et al. "An Outlook on X-Ray CT Research and Development", Medical Physics, 35(3): 1051-1064, Mar. 2008.

(Continued)

*Primary Examiner* — Irakli Kiknadze

(57) ABSTRACT

A CT scanner comprises at least one cone beam x-ray source assembly mounted on a gantry frame, the gantry frame rotatable about a rotation axis, the x-ray source assembly operable to emit a cone beam at an orientation with respect to the rotation axis, and a controller operable to adjust an orientation of the cone beam during a rotation cycle of the gantry, wherein the controller adjusts the orientation to radiate a substantially same volume of interest over the rotation cycle.

27 Claims, 12 Drawing Sheets

(56) References Cited

OTHER PUBLICATIONS

Yu et al. "Cone-Beam Composite-Circling Scan and Exact Image Reconstruction for a Quasi-Short Object", International Journal of Biomedical Imaging, ID 87319, p. 1-10, 2007.

International Preliminary Report on Patentability Dated Oct. 28, 2010 From International of WIPO Re. Application No. PCT/IL2009/000385.

* cited by examiner

CT CONE BEAM SCANNER

RELATED APPLICATIONS

This Application is a National Phase of PCT Patent Application No. PCT/IL2009/000385 having International filing date of Apr. 6, 2009, which claims the benefit of U.S. Provisional Patent Application No. 61/123,938 filed on Apr. 14, 2008. The contents of the above Applications are all incorporated herein by reference.

FIELD OF THE INVENTION

The present invention relates to cone beam Computerized Tomography (CT), and more particularly, but not exclusively, to cone beam CT applied to scan moving objects.

BACKGROUND OF THE INVENTION

CT scanners are used for medical imaging as well as for industrial inspection applications. CT imaging is based on an x-ray source mounted on a rotatable gantry opposite an x-ray detector array. The x-ray source directs an x-ray beam in a direction perpendicular to a rotational axis of the gantry through an object and toward the x-ray detector array as the gantry is rotated. The object is typically centered about the rotational axis of the gantry. The directed x-ray beam partially attenuated by the object impinges on the x-ray detector array to form an x-ray image of the object. Rotating the gantry provides for acquiring a plurality of angular views of the object. Typically an angular span of about 180 degree or more is used for imaging. In helical scanning, the rotating gantry rotates as the object is relatively translated along the rotational axis of the gantry. An image reconstruction processor typically uses filtered back projection or other reconstruction techniques to produce a reconstructed volume image based on the acquired x-ray images.

Fan beam CT scanners employ an x-ray fan beam and a linear detector array. In fan beam CT scanning, a single two-dimensional (2D) image data set, e.g. slice of an object is captured for each rotation of the gantry. Acquiring a 3D data set, one 2D slice at a time is inherently slow. Moreover, in medical applications, motion artifacts occur because adjacent slices are not imaged simultaneously. Also, dose utilization is less than optimal, because the distance between slices is typically less than an x-ray collimator aperture used to project the x-ray beam, resulting in double exposure to many parts of the inspected object. Also known are multi-slice CT scanners employing detectors with multiple rows of detector elements that scan multiple slices at a time. Multi-line CT scanners improve some of these shortcomings to a limited degree.

Cone beam CT scanners include an x-ray source that projects a pyramid shaped x-ray beam opposite a 2D detector array for detecting an area image of the object. With cone beam CT scanners a larger volume of the inspected object is covered over one rotation of the gantry as compared to a fan beam system. With the larger volume coverage per rotation, motion artifacts can be reduced as well as the scanning period required to cover the object. One of the known drawbacks of cone beam CT scanning, as will be described in further detail below, is that the data set collected over a single scan is incomplete. Missing data introduces artifacts during image reconstruction, resulting in images which may be inadequate for, for example, medical diagnosis or part quality determination purposes.

Tuy H., "An inversion formula for cone-beam reconstruction", SIAM Journal of Applied Mathematics 43, 546-552" (1983), the contents of which is incorporated herein by reference, describes a condition for achieving data completeness in cone beam CT scanning that has been widely accepted. In what is known as the Tuy-Smith condition, data completeness is achieved when the source trajectory intersects every plane passing through the reconstructed volume in the scanned object.

A number of source trajectories have been attempted to increase the field of view of the CT scanner and to reduce cone-beam artifacts.

U.S. Pat. No. 5,784,481, entitled "CT cone beam image reconstruction with circle and line scan path" the contents of which is incorporated herein by reference, describes a CT cone beam imaging system that provides relative movement between the cone beam source and the object along a scan path resulting in a helical scan. The relative movement can be provided by linear movement of a patient support member or alternatively by translation of the gantry.

U.S. Pat. No. 7,305,063, entitled "Cylindrical x-ray tube for computed tomography imaging", the contents of which is incorporated herein by reference, describes an x-ray tube with a cylindrical anode that rotates about a longitudinally aligned cylinder axis. Electrons are accelerated toward a selected spot on a target outer surface region of the cylindrical anode. Electrostatic or electromagnetic deflectors sweep the selected spot back and forth across the target outer surface region of the cylindrical anode providing an axial beam sweeping. This provides for distributing heating across a cylindrical anode to improve thermal characteristics of the x-ray tube. One embodiment describes using the beam sweep to provide longitudinal scanning while the subject support remains stationary in cardiac imaging. It is stated that the beam sweep should be coordinated with the angular rotation of the gantry to ensure sufficient angular coverage for each voxel in the image volume. The trajectory described is a helical trajectory along a 12 cm length.

U.S. Pat. No. 6,504,892, entitled "System and method for cone beam volume computed tomography using circle-plus-multiple-arc orbit" the contents of which is incorporated herein by reference, describes a system and method for cone beam volume computed tomography by taking signals along an orbit having a circle plus two more off-axis arcs. The arc data is used to reconstruct data that cannot be recovered from the circle scan.

U.S. Pat. No. 5,712,889 entitled "Scanned volume scanner" the contents of which is incorporated herein by reference, describes a volume CT scanner with a means for generating an electron beam and linearly scanning it along a target to form a succession of cone-shaped x-ray beams. A vane collimator receives the successive cone-shaped x-ray beams and forms a succession of adjacent parallel fan-shaped x-ray beams which successively irradiate adjacent planar slices along the length of a volume of the object to be scanned. A detector array includes a plurality of adjacent longitudinally elongated detector elements extending across each of said beams for receiving the succession of transmitted parallel fan-shaped x-ray beams.

U.S. Pat. No. 5,068,882, entitled "Dual parallel cone beam circular scanning trajectories for reduced data incompleteness in three-dimensional computerized tomography", contents of which is incorporated herein by reference, describes a CT cone beam imaging system for minimizing the incompleteness of the data set acquired. Among other embodiments there is described a system that reduces data incompleteness by using two cone beam x-ray sources offset from each other by 90 degrees with corresponding area detectors. The two sources form two parallel circular trajectories during gantry rotation.

US Patent Application Publication No. 20060285633, entitled "Multiple source CT scanner", the contents of which is incorporated herein by reference, describes a CT scanner including a plurality of cone-beam x-ray sources offset along a CT axis, the axis over which the x-ray source and detector are rotated. A detector is positioned opposite the x-ray sources. The x-ray sources and detector are rotatable about the CT axis. The x-ray sources direct x-rays through the patient that are received by the detector at a plurality of rotational positions, thereby generating projections from the plurality of x-ray sources that are used to construct the three-dimensional CT image of the patient.

International Patent Application Publication No. WO 2006/038145, entitled "Computed Tomography Method", the contents of which is incorporated herein by reference, describes a computed tomography method and apparatus where a focal spot of a cone beam is switched between at least two positions spaced apart from each other and arranged on a line parallel to the axis of rotation to enlarge the reconstructable examination zone parallel to the axis of rotation.

SUMMARY OF THE INVENTION

An aspect of some embodiments of the present invention is the provision of system and method for providing a source trajectory that affords collecting a near complete or complete set volumetric data scanned with a cone beam CT scanner with improved temporal resolution. According to some embodiments of the present invention, complete set volumetric data is scanned during 360 degree scanning and a near complete set volumetric data is scanned during 180 degree scanning. According to some embodiments of the present invention, the trajectory is a non-circular trajectory that is a function of the angular rotation of the gantry. According to some embodiments of the present invention, the orientation of the beam is controlled so as to center the cone beam on the volume of interest along substantially the entire trajectory.

An aspect of some embodiments of the present invention is the provision of a CT scanner comprising: at least one cone beam x-ray source assembly mounted on a gantry frame, the gantry frame rotatable about a rotation axis, the x-ray source assembly operable to emit a cone beam at an orientation with respect to the rotation axis; and a controller operable to adjust an orientation of the cone beam during a rotation cycle of the gantry, wherein the controller adjusts the orientation to radiate a substantially same volume of interest over the rotation cycle.

Optionally, the controller is operable to alter the orientation of the cone beam in a cyclical manner as a function of an angle of rotation of the gantry.

Optionally, the controller is operable to alter a position of a focal spot of the x-ray source assembly in synchronization with an adjustment to the orientation.

Optionally, movement of the focal spot over a cycle of gantry rotation defines an x-ray source trajectory that spans over a plurality of planes perpendicular to the axis of rotation of the gantry.

Optionally, movement of the focal spot along the trajectory is cyclical and has a frequency equal to a frequency of rotation of the gantry or an integer multiple of a frequency of rotation of the gantry.

Optionally, movement of the focal spot over a cycle or integer number of cycles of gantry rotation defines an x-ray source trajectory that is a closed loop trajectory.

Optionally, the controller is operative to move the position of the focal spot linearly in a direction along an axis parallel to the rotational axis of the gantry over a cycle of gantry rotation.

Optionally, the controller is operative to move the position of the focal spot along an arc over a cycle of gantry rotation.

Optionally, the controller is operative to move the position of the focal spot along a circular trajectory having an axis of rotation perpendicular to the gantry axis of rotation over a cycle of gantry rotation.

Optionally, the CT scanner comprises a detector array movably mounted on the gantry and operative to detect radiation from the cone beam, wherein the controller is operative to control movement of the detector array in synchronization with a change in orientation of the cone beam.

Optionally, the CT scanner comprises a collimator movably mounted on the gantry frame, wherein the collimator is operative to orient the cone beam toward the volume of interest.

An aspect of some embodiments of the present invention is the provision of a CT scanner comprising: at least one cone beam x-ray source assembly mounted on a gantry frame rotatable about a rotation axis, operable to emit a cone beam having an orientation with respect to the rotation axis; and a controller operable to change said orientation while the gantry is rotating, wherein the orientation of the cone beam relative to the rotation axis is a function of an angle of rotation of the gantry.

Optionally, the controller is operative to change said orientation with a frequency equal to a frequency of rotation of the gantry or an integer multiple of the frequency of rotation of the gantry.

Optionally, the controller is operative to move a position of a focal spot of the cone beam relative to the gantry frame during gantry rotation, wherein the focal spot position relative to the gantry frame is a function of an angle of rotation.

Optionally, the controller is operative to synchronize with the change in orientation of the cone beam with the movement of the focal spot position.

Optionally, the synchronization provides for radiating a substantially same volume of interest during movement of the focal spot over a rotation cycle of the gantry.

Optionally, movement of the focal spot relative to the gantry frame over a cycle or integer number of cycles of gantry rotation defines an x-ray source trajectory that is a closed loop trajectory.

Optionally, focal spot motion along the trajectory is cyclical and has a frequency equal to a frequency of rotation of the gantry or an integer multiple of a frequency of rotation of the gantry.

An aspect of some embodiments of the present invention is the provision of a CT scanner comprising: at least one cone beam X ray source mounted on a gantry frame, the gantry frame rotatable about a rotation axis, the X ray source including a focal spot from which a cone beam is emitted; and a controller operable to move a position of the focal spot relative to the gantry frame during rotation of the gantry, wherein the movement relative to the gantry frame is a function of an angle of rotation of the gantry and has a frequency equal to a frequency of rotation of the gantry or an integer multiple of a frequency of rotation of the gantry.

Optionally, movement of the focal spot relative to the gantry frame over a cycle of gantry rotation and the rotation of the focal spot with gantry rotation defines an x-ray source trajectory that spans over a plurality of planes perpendicular to the axis of rotation.

Optionally, the x-ray source trajectory is a closed loop trajectory.

Optionally, the controller is operative to move the position of the focal spot in a direction along an axis parallel to the rotational axis of the gantry.

Optionally, the controller is operable to adjust an orientation of the cone beam toward a substantially same volume of interest during a rotation cycle of the gantry.

Optionally, the orientation is defined as function of the position of the focal spot relative to the gantry frame and adjusting the orientation according to the function provides for radiating the substantially same volume of interest as the position of the focal spot changes.

Optionally, the controller is operative to synchronize detection of the cone beam array with a position of the focal spot.

Optionally, synchronization provides for cone beam detection over a full extent of translation of the focal spot during a partial scan.

Optionally, the x-ray source assembly is movably mounted on the gantry frame, and wherein moving the position of the focal spot is provided by moving the position of the x-ray source assembly.

Optionally, moving the position of the focal spot with respect to the gantry frame is provided by sweeping an electron beam of the x-ray source assembly relative to an anode of the x-ray source assembly.

Optionally, moving the position of the focal spot is provided by moving a cathode of the x-ray source assembly relative to an anode of the x-ray source assembly.

Optionally, the CT scanner comprises multiple x-ray source assemblies mounted on the gantry frame, wherein at one assembly provides for focal spot translation relative to the gantry frame.

Optionally, the controller is operable to asynchronously move a focal spot of each assembly during gantry rotation.

Optionally, the controller is operative to synchronize detection of the cone beam array with a signal from a heart beat monitor.

An aspect of some embodiments of the present invention is the provision of a method for CT scanning, the method comprising: aligning a cone beam x-ray source to cover a volume of interest within a region enclosed by a gantry frame, wherein said volume of interest is generally centered about the gantry rotation axis; rotating the cone beam source around the volume of interest about a rotation axis; moving the cone beam x-ray source along a defined trajectory during said rotation, wherein the trajectory includes a component of translation in the direction of the axis of rotation; and adjusting orientation of the cone beam x-ray source to consistently point toward the volume of interest over the defined trajectory.

Optionally, the defined trajectory is a function of angular rotation of the gantry.

Optionally, the defined trajectory spans over a plurality of planes.

Optionally, the defined trajectory is a closed loop trajectory over a cycle of gantry rotation.

Optionally, the defined trajectory is cyclical and has a frequency equal to a frequency of rotation of the gantry or an integer multiple of a frequency of rotation of the gantry.

Optionally, the trajectory includes a component of translation in a direction along an axis parallel to the rotational axis of the gantry.

Optionally, the trajectory includes a circular trajectory parallel to the rotational axis of the gantry.

In various embodiments of the invention the invention wherein moving comprises moving a focal spot within an x-ray tube by electrostatic or magnetic means or by moving the x-ray tube mechanically.

Optionally, moving is responsive to a signal from a heart monitor.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
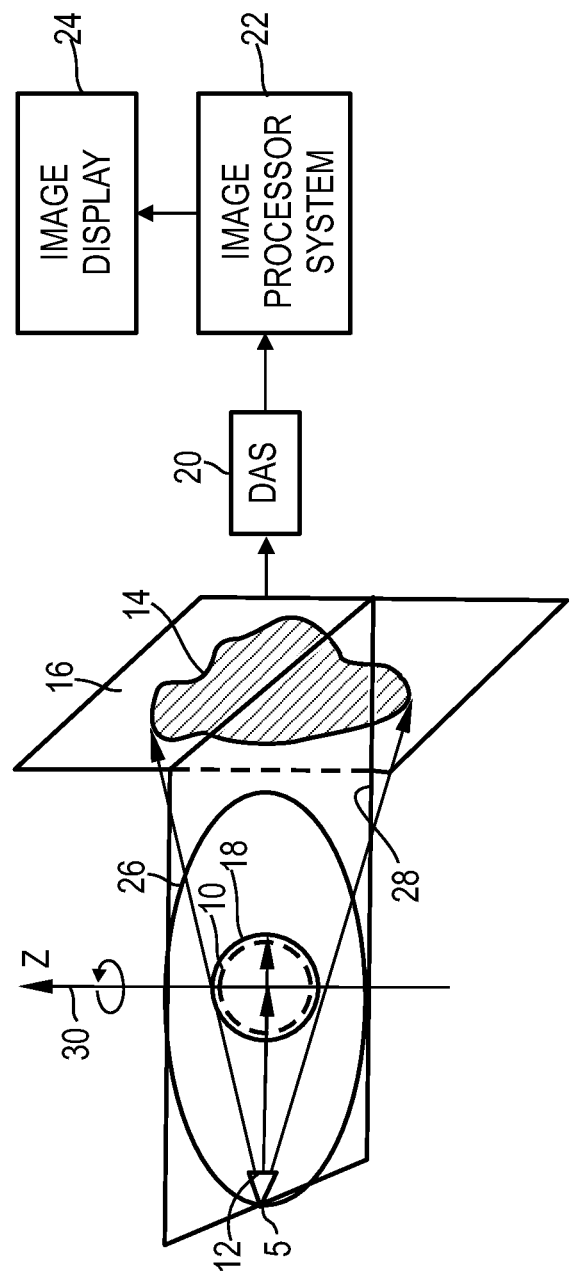
FIG. 1 is schematic illustration of conventional cone beam CT scanning geometry.

The present invention relates to cone beam Computerized Tomography (CT), and more particularly, but not exclusively, to cone beam CT for scanning moving objects.

A problem in conventional circular trajectory cone beam scanners is data incompleteness which typically leads to artifacts in image reconstruction. Data incompleteness occurs since there are planes through the reconstructed volume which are approximately parallel to the source trajectory and thereby do not intercept the source trajectory as is required by the Tuy-Smith condition.

While helical (or spiral) scanning may provide for reduced data incompleteness for substantially large volumes, e.g. larger than a volume covered by a cone beam angle, this method has poor temporal resolution which is a disadvantage for some applications such as cardiac imaging where the heart is in motion. Another disadvantage when scanning relatively small volumes is that in helical scanning the beam covers different parts of the volume of interest (less than the entire volume of interest) as the beam is translated in a direction parallel to the axis. The present inventors have found that imaging only part of the volume of interest at a time reduces the temporal resolution and causes artifacts in image reconstruction. In cardiac helical imaging, different parts of the heart are imaged during different heart beats. The present inventors have found that data acquired in helical scanning is often inadequate for cardiac imaging for at least the above reasons.

In cardiac imaging a fast single shot imaging of the entire heart volume is desired. In some applications 180 degrees scanning (as compared to 360 degrees scanning) is desirable for cardiac imaging due to temporal artifacts of the beating heart. However, data incompleteness and image artifacts are far more severe for 180 degree scanning than for 360 degree scanning by a cone beam scanner.

An aspect of some embodiments of the present invention provides for moving a position of the x-ray source and/or focal spot of an x-ray source assembly relative to the gantry frame while the gantry is rotating such that the movement relative to the gantry frame is a function of an angle of rotation of the gantry. According to some embodiments of the present invention, the overall trajectory of the focal spot over a rotation of the gantry is a non-circular trajectory that satisfies or nearly satisfies the Tuy-Smith condition for 360 degree rotation and provides for reduce data incompleteness for 180 degree rotation. According to some embodiments of the present invention, the overall trajectory of the focal spot spans over more than one plane. According to some embodiments of the present invention, the trajectory of the focal spot relative to the gantry frame is along an axis parallel to the axis of the gantry rotation (i.e., on a cylinder centered at the axis of rotation). According to some embodiments of the present invention, the movement of the focal spot relative to the gantry frame includes at least one back and forth motion of the focal spot over a full gantry rotation so that a position of the focal spot relative to the gantry frame is at a same position after a full cycle gantry rotation, e.g. 360 degree rotation. In some exemplary embodiments, the focal spot is rotated about a rotation axis perpendicular to the rotation axis of the gantry in addition to being rotated with the gantry. According to some embodiments of the present invention the trajectory of the focal spot relative to the gantry frame has a frequency that is equal to a frequency of rotation of the gantry or an integer multiple of a frequency of rotation of the gantry. The source trajectories in embodiments of the present invention may be designed according to the volume of interest designated for reconstruction such that any or nearly any plane passing through the reconstructed volume intersects with the source trajectory and the Tuy-Smith condition is met or nearly met.

According to some embodiments of the present invention, an orientation of the cone beam is controllably adjusted as the position of the focal spot moves along an axis parallel to the axis of rotation. According to some embodiments of the present invention, the orientation of the cone beam is adjusted to direct the cone beam toward a same volume of interest from substantially each point in the focal spot trajectory, e.g. a trajectory including translation in a direction of rotational axis of the gantry. According to some embodiments of the present invention, adjusting the orientation of the cone beams provides for substantially covering a same volume of interest over the focal spot trajectory. According to some embodiments of the present invention, adjusting the orientation of the cone beam provides for directing the cone beam toward the volume of interest from a plurality of angles with respect to the axis of rotation. The present inventors have found that substantially centering the cone beam on volume of interest throughout the focal spot trajectory serves to increase the data acquired for reconstruction, e.g. reduce data incompleteness without increasing exposure.

According to some embodiments of the present invention, adjustment in cone beam orientation is provided by a collimator, e.g. a dynamic collimator that is operative to follow the focal spot position as it moves and change the orientation of the cone beam as its focal spot moves. According to some embodiments of the present invention, the x-ray sources is associated with a collimator that is operable to controllably direct, e.g. orient, the X ray beam toward a volume of interest from a plurality of points along the non circular source trajectory, e.g. to follow the X ray source motion parallel to the rotation axis. According to some embodiments of the present invention, the collimator is operable to direct the x-ray beam towards a detector that is fixedly mounted on the gantry from a plurality of points along the focal spot trajectory. According to some embodiments of the present invention adjustment in cone beam orientation is provided by mechanical tilting of an x-ray tube moveable mounted on a gantry.

According to some embodiments of the present invention, movement, e.g. sweeping of the focal spot in relation to the gantry frame can be provided by mechanical and/or electronic means. In some exemplary embodiments, movement of the focal spot relative to the gantry frame is provided by movably mounting an x-ray source assembly, e.g. an x-ray tube on the gantry frame and controlling movement of the x-ray source assembly relative to the gantry frame during gantry rotation. In some exemplary embodiments, movement of the focal spot relative to the gantry frame is provided by mechanically moving a cathode of the x-ray source assembly. In some exemplary embodiments, movement of the focal spot relative to the gantry frame is provided by electronically deflecting an electron beam by magnetic steering. Since the focal spot trajectory includes back and forth motion of the focal spot in the axial direction over one rotation cycle, the velocity of movement along the trajectory may typically be substantially faster than translation velocity in helical scanning. The present inventors have found that displacing one of the x-ray tube, cathode and/or deflecting the electron beams (as opposed to translating a gantry frame and/or the patient support structure) provides for faster and more readily controllable movement of the focal spot along a designated trajectory due to weight considerations. In some exemplary embodiments, focal spot displacement based on cathode displacement and/or electronic deflection of the electron being is advantageous in this respect.

According to some embodiments of the present invention, a detector for detecting radiation emitted by the x-ray source and attenuated by the volume of interest is moveably mounted on the gantry frame and is moved in synchronization with movement of the focal spot with respect to the gantry frame. According to other embodiments of the present invention, the detector is fixedly mounted on the gantry frame and includes an area of detection that provides for detecting cone beams emitted from the different positions of the focal spots along the focal spot trajectory with respect to the gantry frame.

According to some embodiments of the present invention, the focal spot trajectory relative to the patient is provided by translating the gantry back and forth in a direction along an axis parallel to the rotational axis over a single gantry rotation. In some exemplary embodiments, the focal spot trajectory is provided by translating the patient support member back and forth over a single gantry rotation cycle. According to some embodiments of the present invention, the trajectory provides for a plurality of non-perpendicular cutting planes.

According to some embodiments of the present invention, an x-ray source is rotatably mounted on the gantry so as to provide rotational focal spot trajectory on a plane perpendicular to the rotational axis of the gantry. According to some embodiments of the present invention, a detector is likewise rotatably mounted on the gantry so as to provide rotation on a plane perpendicular to the rotational axis of the gantry in synchronization with rotation of the x-ray source.

According to some embodiments of the present invention, a plurality of x-ray sources are mounted on a gantry frame for radiating a volume of interest. In some exemplary embodiments the different x-ray sources are displaced along a direction of the axis of rotation. In some exemplary embodiments, each of the x-ray sources radiate in turn toward a single detector. According to some embodiments of the present invention, the collimator (or several collimators) is operable to direct the x-ray beam from a plurality of x-ray sources towards a single detector.

Reference is now made to FIG. 1, is schematic illustration of conventional cone beam CT scanning geometry. A cone beam x-ray source 12 is positioned to irradiate object 10 contained within a spherical volume 18, and to thereby project cone-beam data representing an image 14 onto an associated planar detector array 16, comprising a matrix array of discrete detector elements (not shown in detail). Optionally detector array 16 may be spherical or arc shape detector which is centered about a focal spot of the cone beam projected toward it.

Gantry rotation provides for a circular orbit of motion 26 for the cone beam source 12 around the object 10, the circular orbit lying in a mid-plane 28, i.e. a plane passing through the center of sphere 18. In a typical arrangement, detector array 16 is constrained to move with source 12, so that object 10 remains positioned between source 12 and detector array 16. Cone-beam projection data is acquired by detector array 16 for successive positions and/or view angles of source 12, as source 12 traverses the circular orbit 26. A Z-axis 30 passes through the object 10, in orthogonal relationship with mid-plane 28, and intersects the mid-plane at substantially a center of spherical volume 18.

The cone-beam projection data is in the form of x-ray photons that penetrate the object and are sensed by the respective detector elements, of detector array 16. Thus, planar detector 16 provides cone beam projection data in analog form. Such data is coupled to a Data Acquisition System (DAS) 20, which samples analog data from the respective detector elements and converts the data to digital form for subsequent processing. The digitized projection data is coupled to an image reconstruction processor system 22, which operates on the projection data in accordance with the invention, as described hereinafter, to reconstruct an image of the object 10. The reconstructed image may be presented in viewable form, for example, by means of an image display 24.

Figure 2:
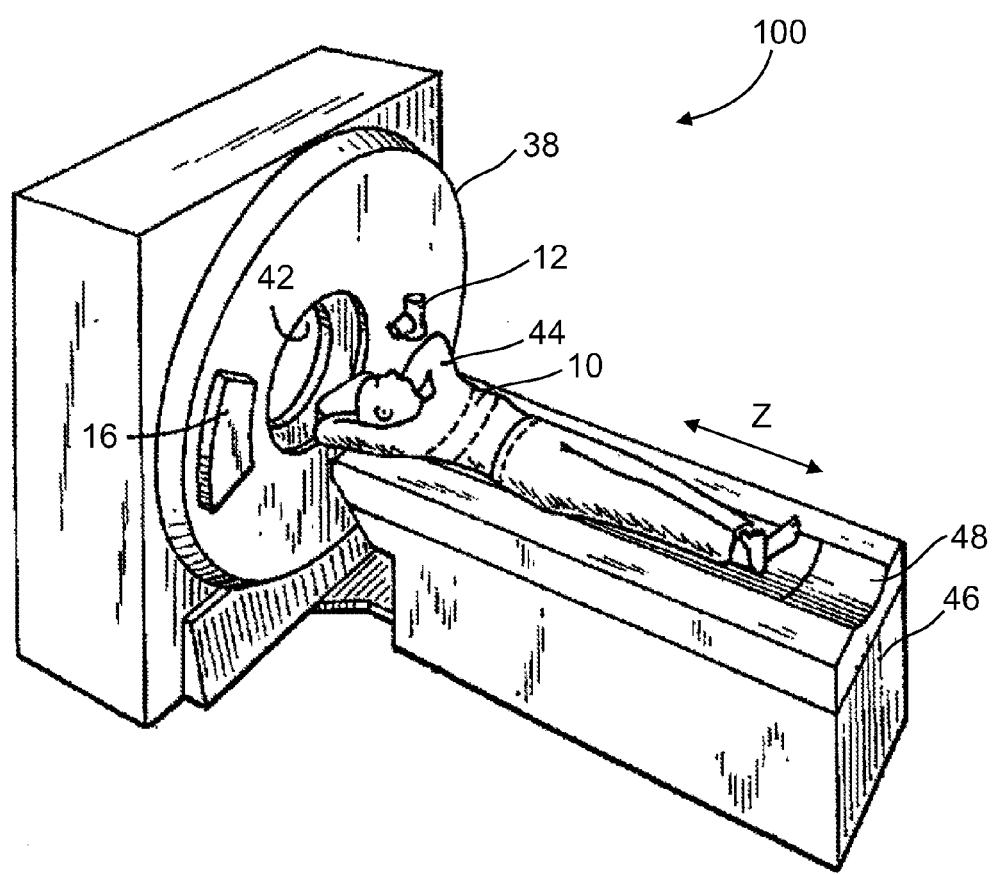
FIG. 2 is a schematic illustration of a conventional CT imaging system for use in some embodiments of the present invention.

Reference is now made to FIG. 2 showing a schematic illustration of a conventional prior art CT imaging system 100. In conventional CT imaging systems a source 12 and detector array 16 mounted on rotatable gantry 38, on opposing sides of the bore 42. Typically a subject 44 is positioned on table support 46 and may be inserted to the bore by linear motion of member 48 so that a volume of interest 10 is generally centered on the axis of rotation. Gantry rotation speed may typically be 0.5 rotation/sec or 1 rotation/sec or 2 rotation/sec. However faster systems approaching 4 rotations/sec are known in the art, as well as slower systems.

Accordingly, a circular orbit 26, as described above, is provided by rotation of gantry 38 with source 12. The volume of interest 10 is covered by a single rotation provided the cone beam from source 12 is sufficiently wide to cover volume 10. As described hereinabove, the data from such scan suffers from incompleteness and image artifacts.

Figure 3A:
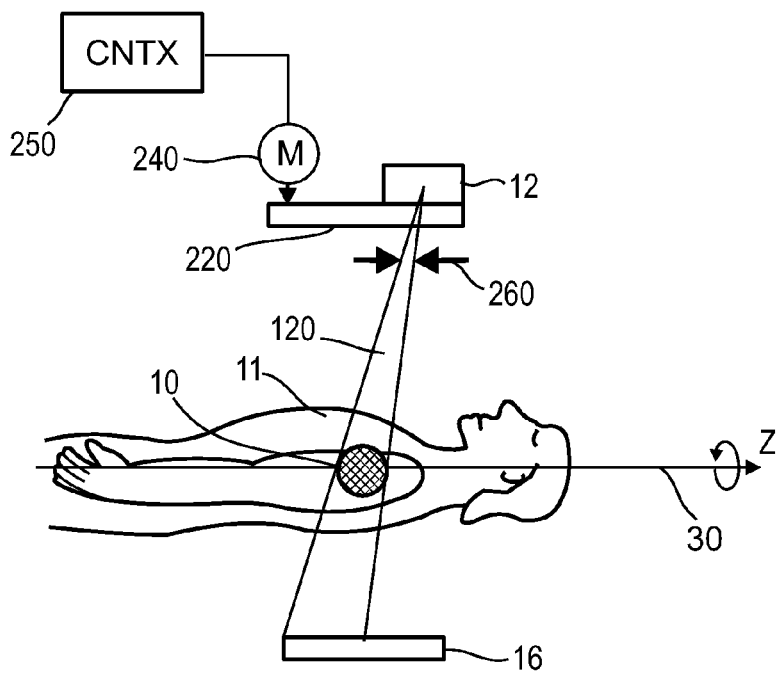
FIGS. 3A-3B is a schematic illustration of an x-ray source movably mounted on a rotatable gantry in accordance with some embodiments of the present invention.
Figure 3B:
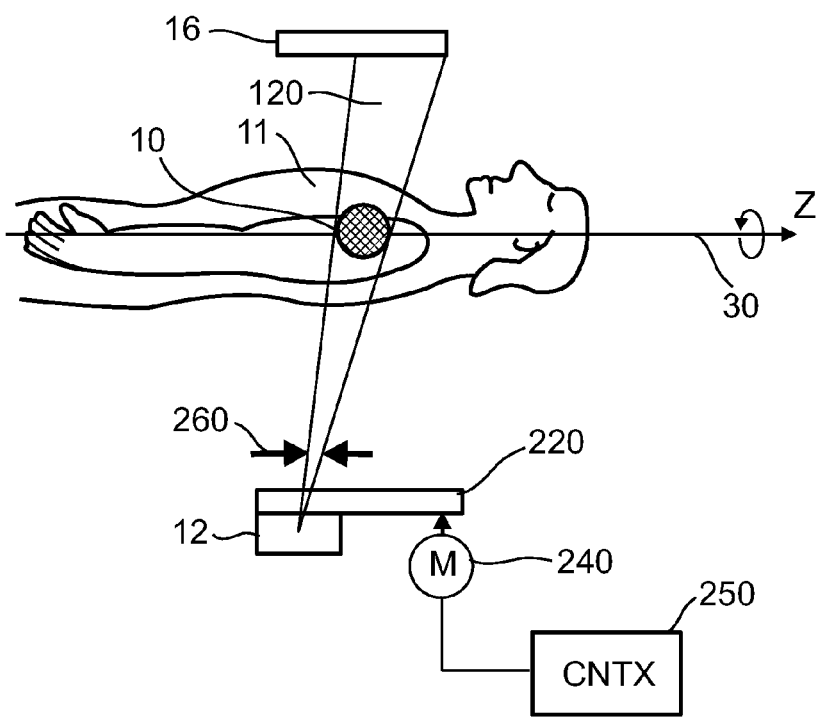

Reference is now made to FIGS. 3A and 3B showing a schematic illustration of an x-ray source movably mounted on a rotatable gantry in accordance with some embodiments of the present invention. According to some embodiments of the present invention, x-ray source 12, e.g. x-ray tube is movably mounted on gantry 38 (FIG. 2) with linear rail 220 and is capable of moving along an axis parallel to the rotation axis, e.g. Z axis, responsive to a motor 240 and controller 250. According to some embodiments of the present invention arc rails are provided such that the distance between the source 12 and the center of volume 10 stays constant while the source is translated. According to some embodiments of the present invention a collimator 260, collimates the x-ray radiation from x-ray source 12 so that cone beam 120 is substantially centered on a volume of interest 10 and is detected by a detector 16. In some exemplary embodiments, x-ray source is tiltably and/or rotatably mounted on gantry 38, and orientation of the cone beam is provided by controllably tilting and/or rotating x-ray source 12, e.g. x-ray tube. In some exemplary embodiments detector 16 is arc shaped. In some exemplary embodiments, controller 250 in communication with a motor (not shown) is operative to control tilting and rotation of x-ray source 12.

FIGS. 3A and 3B show two exemplary positions of x-ray source 12 as gantry 38 rotates by 180 degrees. In some exemplary embodiments, x-ray source is positioned on one end of range of motion provided by linear rail 220 (FIG. 3A) and after a 180 degree rotation, the x-ray source 12 is positioned at an opposite end of the range of motion of linear rail 220 (FIG. 3B). According to some embodiments of the present invention, collimator 260 is operative to adjust the direction and/or orientation of cone beam 120 so that cone beam 120 is generally centered on volume of interest 10 as the x-ray source is translated back and forth along linear ray 220. According to some embodiments of the present invention, the trajectory of x-ray source 12 is periodic and is associated with the frequency of gantry rotation.

According to some embodiments of the present invention, collimator 260 moves together with the x-ray source 12 and/or is integrated with x-ray source 12 as a single unit. Typically, collimator 260 includes two or more blades operative to direct the orientation of cone beam 120. According to some embodiments of the present invention, controller 250 is operative to move the blades in synchronous with motion of the x-ray source 12 so as direct and/or center cone beam 120 toward the volume of interest from substantially every point of the source trajectory.

According to some embodiments of the present invention, detector 16 spans a larger surface area than the surface area of cone beam 120 and only a part of detector 16 is radiated by beam 120 at any source position. In some exemplary embodiments, the portion of the detector that is radiated is known based on the known trajectory of the source and only data from the detector that is radiated by cone beam 120 at any given time is acquired and stored. According to some embodiments of the present invention, acquiring and storing data only from a portion of detector 16 that is radiated at any given time provides for reducing memory and processing power required for image construction.

Figure 4:
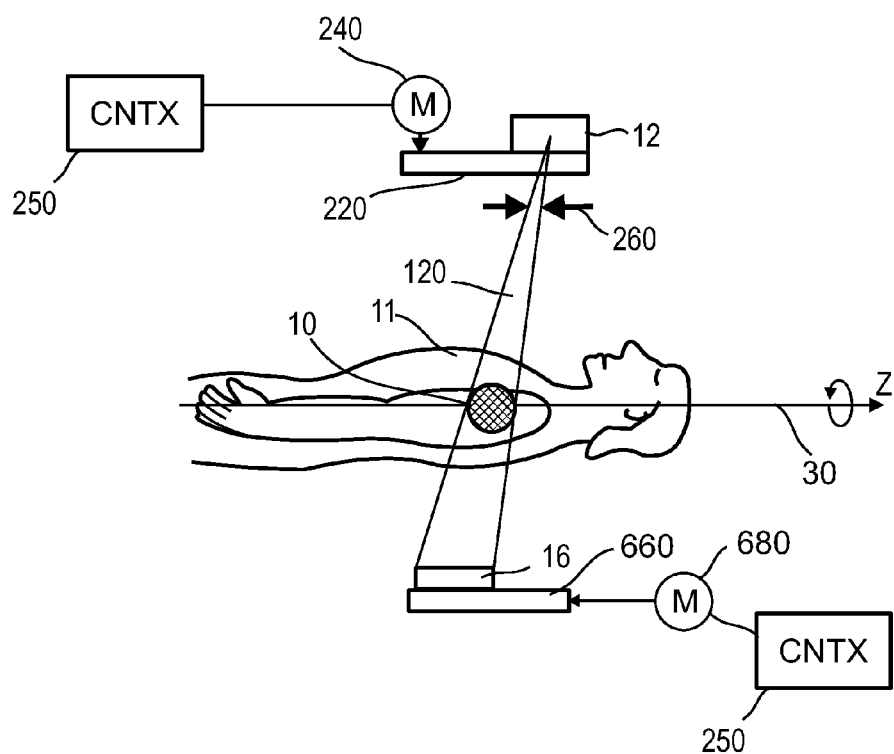
FIG. 4 is a schematic illustration of an x-ray source and a detector movably mounted on a rotatable gantry in accordance with some embodiments of the present invention.

Reference is now made to FIG. 4 showing a schematic illustration of an x-ray source and a detector movably mounted on a rotatable gantry in accordance with some embodiments of the present invention. According to some embodiments of the present invention, detector 16 is translated along a trajectory that provides for detecting cone beam 120 attenuated by volume 10 from every point along the source trajectory. In some exemplary embodiments, a trajectory of detector 16 follows a line of sight of cone beam 120. Typically the trajectory of detector 16 is different than that of the source due to the change of orientation of the cone beam over the source trajectory. Typically, the trajectory of detector 12 will have a same frequency but opposite phase as compared to a trajectory of x-ray source 12 and will be synchronized with motion of x-ray source 12. According to some embodiments of the present invention, controller 250 is operative to synchronize movement of detector 16 and x-ray source 12. According to some embodiments of the present invention, translating detector 16 to follow moving cone beam 120 provides for reducing the size of detector 16 to span substantially a same surface area as a surface area of cone beam 120 attenuated by volume 10 and thereby reducing cost of detector 16 and processing power required for detection.

Figure 5A:
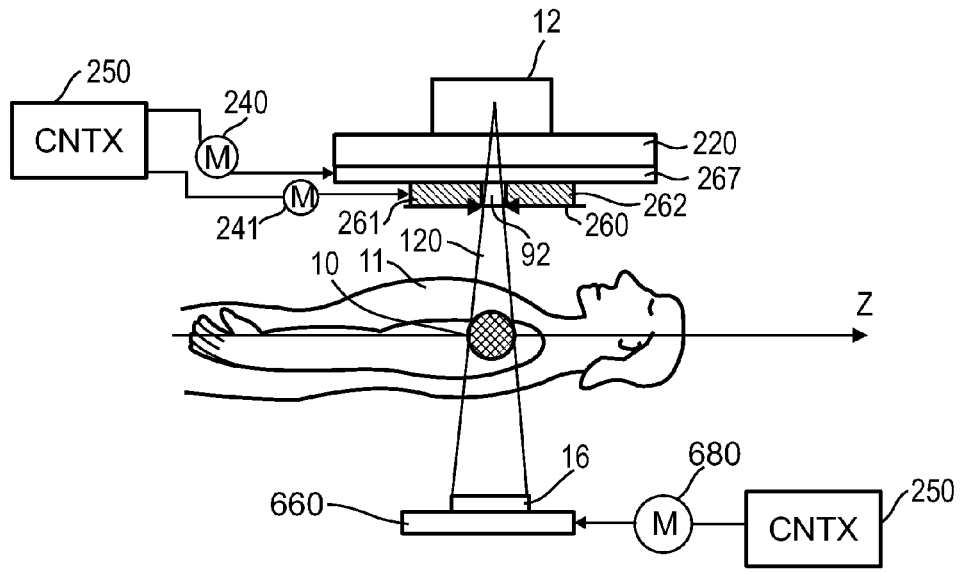
FIGS. 5A-5C are schematic illustrations of collimator positioning with respect to the x-ray source and detector as the source moves with respect to the gantry in accordance with some embodiments of the present invention.
Figure 5B:
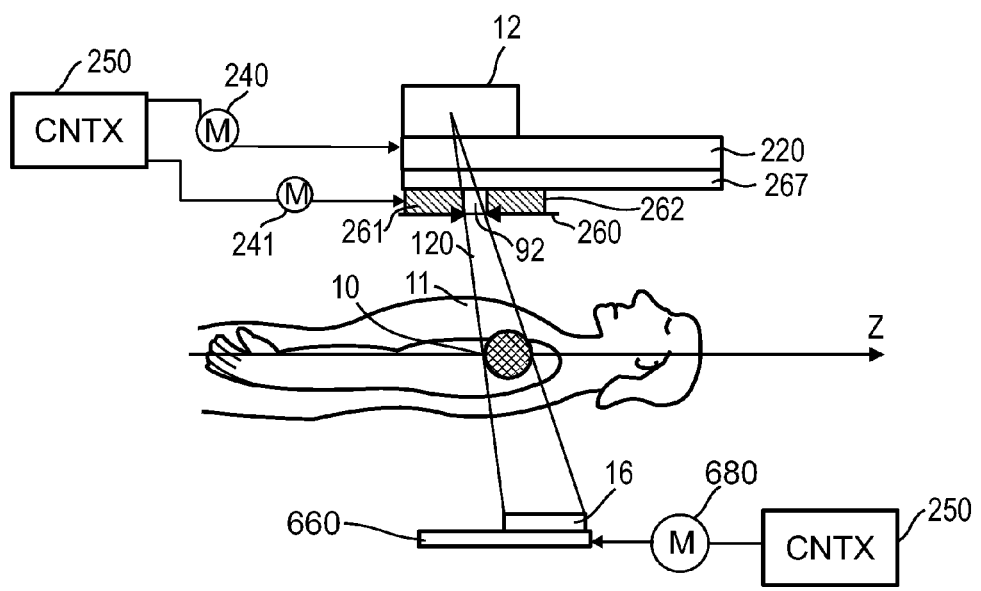
Figure 5C:
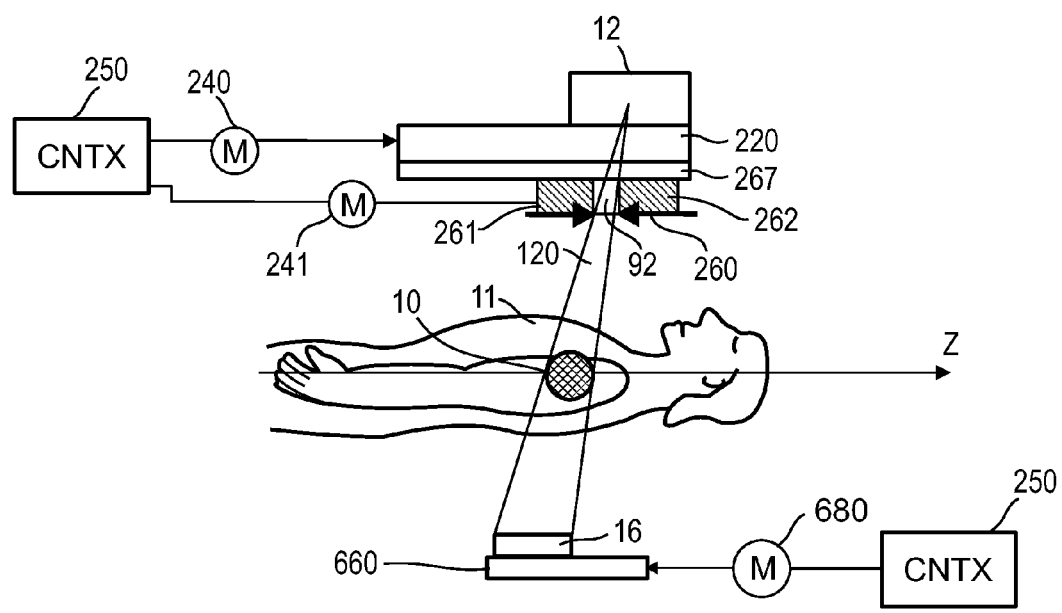

Reference is now made to FIGS. 5A-5C which are schematic illustrations of collimator positioning with respect to the x-ray source and detector as the source moves with respect to the gantry in accordance with some embodiments of the present invention. According to some exemplary embodiments, collimator 260 is mounted on support frames (not shown) that provide for motion with respect to rails 267 and includes blades 261 and 262 with a gap 92 therebetween. According to some embodiments of the present invention, the collimator moves along rails 267 responsive to a motor 241, and controller 250. In some exemplary embodiments, x-ray source 12 is translated along rails 220 responsive to motor 240 and controller 250. Optionally, detector 16 along rails 660 responsive to motor 680 and controller 250. In some exemplary embodiments, position controllers are used to provide accurate positioning of x-ray source 12, collimator 260 and detector 16. According to some embodiments of the present invention, controller 250 is operative to synchronize motion of x-ray source 12, collimator 260 and detector 16. In some exemplary embodiments, rail 660 is arc shaped.

In FIG. 5A, detector 12, gap 92, volume of interest 10 and detector 16 are all aligned such that a mid-plane of cone beam 120 happens to be perpendicular to the gantry rotational axis Z.

In FIG. 5B, x-ray source 12 is translated in one direction (to the left) and collimator 260 follows in the same direction as x-ray source 12 but with a smaller amplitude of translation so that cone beam 120 is tilted in the opposite direction of motion. According to some embodiments of the present invention, tilting of the cone beam provides for covering a same volume of interest is displaced and/or for substantially centering cone beam on volume of interest 10 as the x-ray source. In some exemplary embodiments, detector 16 is also translated but in an opposite direction from x-ray source 12 and collimator 260.

In FIG. 5C, x-ray source 12 is translated in an opposite direction from that shown in FIG. 5B (to the right) and collimator 260 follows in the same direction as x-ray source 12 but with a smaller amplitude of translation so that cone beam 120 is tilted in the opposite direction of motion. According to some embodiments of the present invention, tilting of the cone beam provides for covering a same volume of interest is displaced and/or for substantially centering cone beam on volume of interest 10 as the x-ray source. In some exemplary embodiments, detector 16 is also translated but in an opposite direction from x-ray source 12 and collimator 260.

Figure 6:
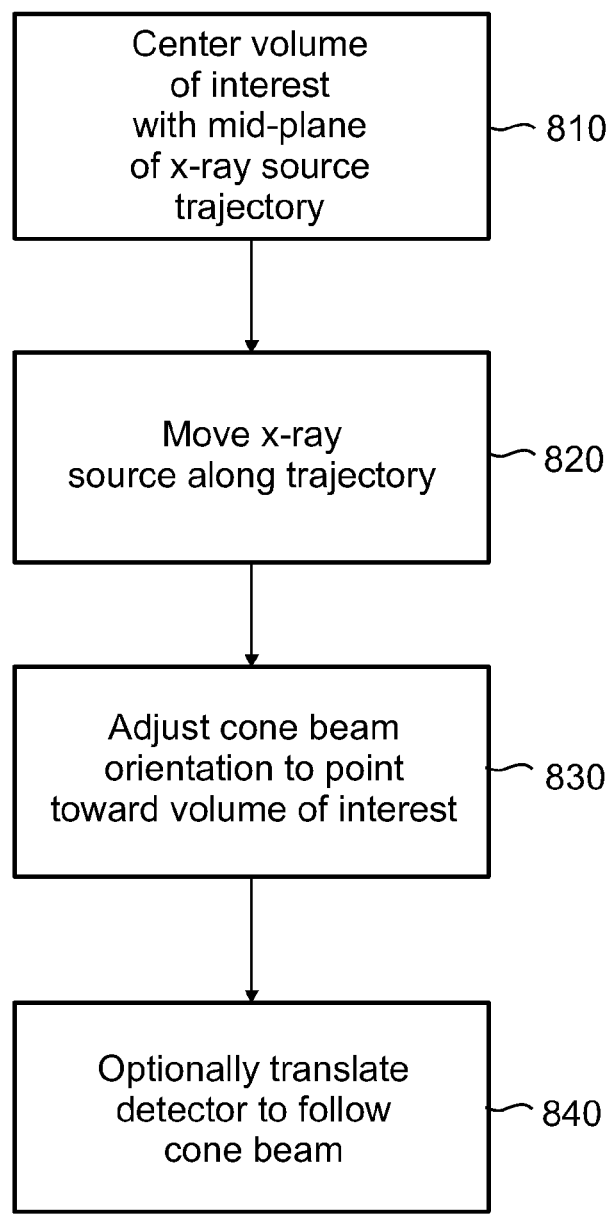
FIG. 6 is an exemplary flow chart of a method for scanning a volume of interest in accordance with to some embodiments of the present invention.

Reference is now made to FIG. 6 showing an exemplary flow chart of method for scanning a volume of interest in accordance with some embodiments of the present invention. According to some embodiments of the present invention, on the onset of scanning the scanned subject is positioned so the volume of interest, e.g. the heart, is generally centered at the crossing of the rotation axis and the mid plane of the source trajectory (block 810). In some exemplary embodiments, an x-ray source is aligned with a volume of interest, e.g. a heart, so that a line of sight of the cone beam is substantially centered with the volume of interest. According to some embodiments of the present invention, the x-ray source, e.g. an x-ray tube and/or a focal spot of the cone beam, is translated over a pre-defined trajectory (block 820). During translation, the subject is irradiated and attenuation data is acquired. In some exemplary embodiments, the trajectory is a closed loop trajectory over one cycle of gantry rotation, e.g. the x-ray source returns to its initial position at the completion of 360° rotation. In some exemplary embodiments, the trajectory spans over rotation of 180° or more but typically less than 360°. According to some embodiments of the present invention, as the x-ray moves along a pre-defined trajectory, an orientation of the cone beam is adjusted to point toward a same volume of interest (block 830). In some exemplary embodiments, change in orientation is provided by translating a collimator along with the x-ray source but with a lag. In some exemplary embodiments, change in orientation is provided by controllably tilting an x-ray tube. According to some embodiments of the present invention, in substantially every position of the x-ray source along the pre-defined trajectory, the cone beam, e.g. a line of sight of the cone beam or center plane of the cone beam, is substantially centered on the volume of interest so that it radiates a substantially same volume of interest. In some exemplary embodiments, a detector is additionally translated along a pre-defined trajectory in synchronization with the trajectory of the x-ray source so as to follow changes in position and orientation of the cone beam (block 840).

Figure 7A:
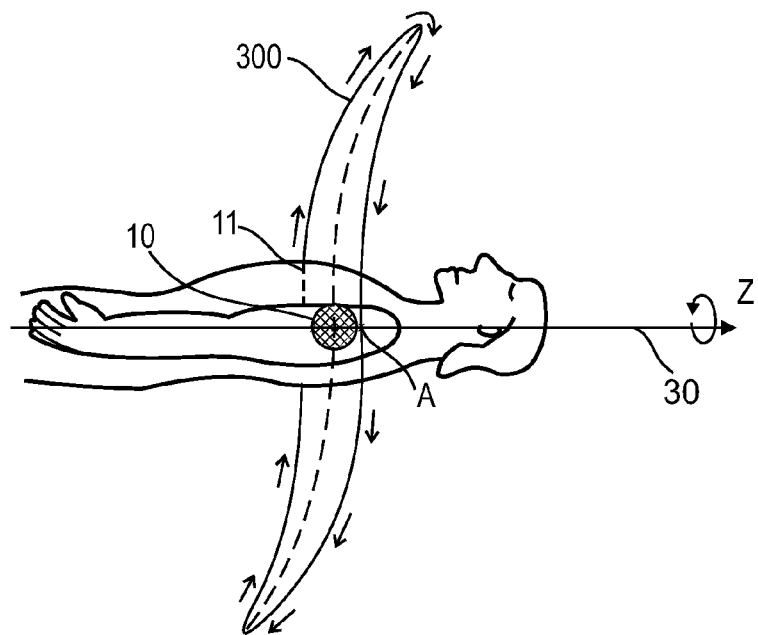
FIGS. 7A-7C are schematic illustrations of three different source trajectories in accordance with some embodiments of the present invention.
Figure 7B:
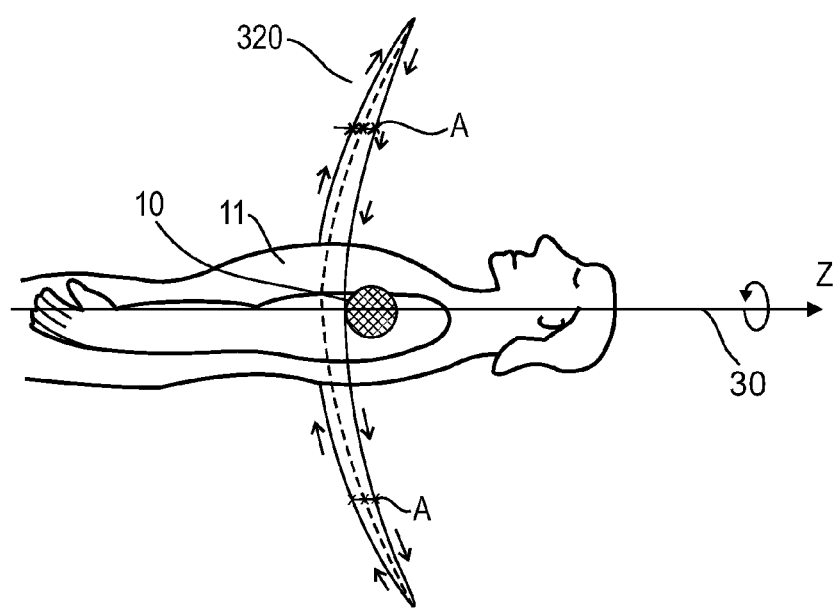
Figure 7C:
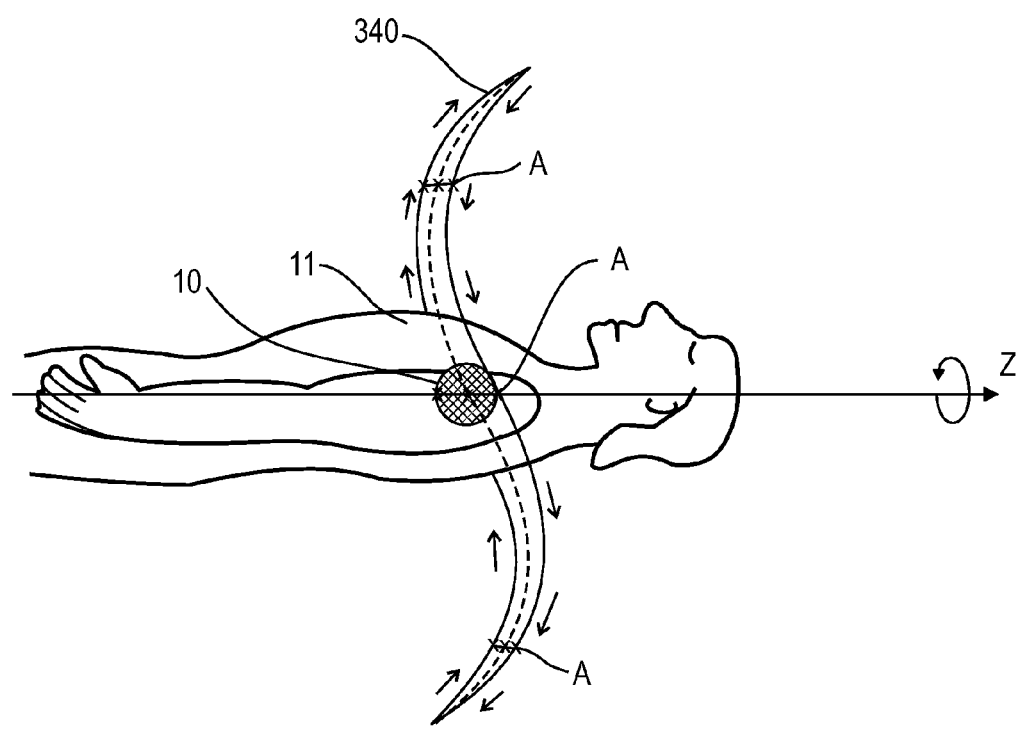

Reference is now made to FIGS. 7A, 7B, and 7C, showing three exemplary source trajectories according to some embodiments of the present invention. It is noted that source trajectory 300, 320, and 340 shown in FIGS. 7A, 7B, and 7C, are shown a slightly isometric manner so as to show the cyclic and close loop nature of the source motion over one rotation of the gantry, however it is understood that the source follows the same trajectory in both the forward and backwards motion along the Z axis, such that the projection of the trajectory (shown in dotted line) is the same for each direction. Points 'A' along the trajectory (shown on both the projected trajectory and the isometric representation) correspond to points where a center plane of the cone beam is perpendicular to the axis of gantry rotation 30.

FIG. 7A schematically illustrates an exemplary x-ray source trajectory 300 over one gantry rotation, e.g. 360 degree rotation, for scanning volume of interest 10 according to some embodiments of the present invention. According to some embodiments of the present invention, source trajectory 300 is obtained when a gantry angle dependent position of x-ray source 12 along the Z direction is a defined by the function:

$$P(\text{source})=P_o \cos^3(\omega t+\phi);$$

Wherein

P is the Z position of the source, e.g. the focal spot of the cone beam, with respect to the axis of rotation, $P_o$ is an initial position of the source and/or focal spot at the onset of gantry rotation;

ω is angular frequency of the gantry;

t is time; and

φ is a phase factor.

According to some embodiments of the present invention, trajectory 300 is adapted for scans of 360 degrees and more but may also be suitable for scans between 180 degrees to 360 degrees, e.g. partial scans. The present inventors have found that trajectory 300 may substantially meet the Tuy-Smith condition for 360 degree rotation so that cone beam artifacts can be substantially eliminated. The present inventors have also found that trajectory provides for reducing data incompleteness and cone beam artifacts for partial scans, e.g. scans between 180 degrees and 360 degrees.

Partial scans typically applied for cardiac imaging to reduce temporal artifacts occurring due to heart motion. The disadvantage in partial scans is increased artifacts due to data incompleteness. The present inventors have found that data incompleteness can be further reduced in partial scans by synchronizing the acquisition of data from the detector and x-ray source motion (over trajectory P(source)) so as to cover the full translation along the Z axis during the scan. For cardiac imaging where the temporal resolution is important, temporal artifacts can be further reduced by performing the scan substantially during a cardiac phase including minimal motion of the heart. According to some embodiments of the present invention, temporal resolution is improved and data incompleteness is reduced by synchronizing the onset of scanning with a monitor signal, e.g. ECG monitor signal and with motion along the P(source) trajectory so as to cover the full translation along the Z axis over a phase in the heart cycle wherein heart motion is minimized, e.g. the diastole phase.

FIG. 7B schematically illustrates another exemplary x-ray source trajectory 320 over one gantry rotation for scanning volume of interest 10 according to some embodiments of the present invention. According to some embodiments of the present invention, source trajectory 320 is obtained for a gantry angle dependent position of x-ray source 12 along the Z direction defined by the function:

$$P(\text{source})=P_o \cos(2\omega t+\phi);$$

wherein:

P is the Z position of the source or the focal spot with respect to the axis of rotation;

$P_o$ is an initial position of the source and/or focal spot at the onset of gantry rotation;

ω is angular frequency of the gantry;

t is time; and

φ is a phase factor.

According to some embodiments of the present invention, any partial scan between 180 degrees to 360 degrees covers the full translation of the source along the Z axis. As such a cardiac scan can be performed wherein the acquisition is responsive to a monitoring signal, e.g. an ECG signal, while the position of the X ray source with respect to the Z axis is not necessarily synchronized with heart beat monitor signal. Although the trajectory shown in FIG. 7B does not meet the Tuy Smith condition for 180 degree scan, it reduces the incompleteness compared to a conventional circular trajectory. Typically, the minimum scan angle is 180 degrees plus "fan" where "fan" is the in-plane beam angle.

FIG. 7C schematically illustrates yet another exemplary x-ray source trajectory 340 over one gantry rotation for scanning volume of interest 10 according to some embodiments of the present invention. According to some embodiments of the present invention, source trajectory 340 is obtained for a gantry angle dependent position of x-ray source 12 along the Z direction defined by the function:

$$P(\text{source})=P_o \cos(3\omega t+\phi);$$

wherein:

P is the position of the source, e.g. the focal spot of the cone beam, with respect to the axis of rotation of the gantry;

$P_o$ is an initial position of the source and/or focal spot at the onset of gantry rotation;

ω is angular frequency of the gantry;

t is time; and

φ is a phase factor.

According to some embodiments of the present invention, the x-ray source follows a defined trajectory, e.g. trajectories 300, 320 and 340, spanning a plurality of planes. It is noted that although FIGS. 7A-7C describe three close looped trajectories, these trajectories are exemplary and other close looped trajectories that are a function of ω are within the scope of the present invention. In some exemplary embodiments, more than one gantry rotation is employed to acquire scan data, e.g. to collect more statistics. In some such embodiments the source trajectory is designed to form a closed loop after an integer number of rotations, e.g. corresponding to the number of gantry rotations employed, as opposed to just after one rotation.

In some embodiments of the invention, the gantry rotates and the source moves periodically even when radiation is not needed with the radiation being turned on just for the duration of one scan, either at any phase of the trajectory or at a particular phase. In another embodiment, the gantry still rotates ahead of the scan (since it takes time to bring it to speed) but the source is made to move just when radiation is turned on, only for the duration of the scan.

Figure 8:
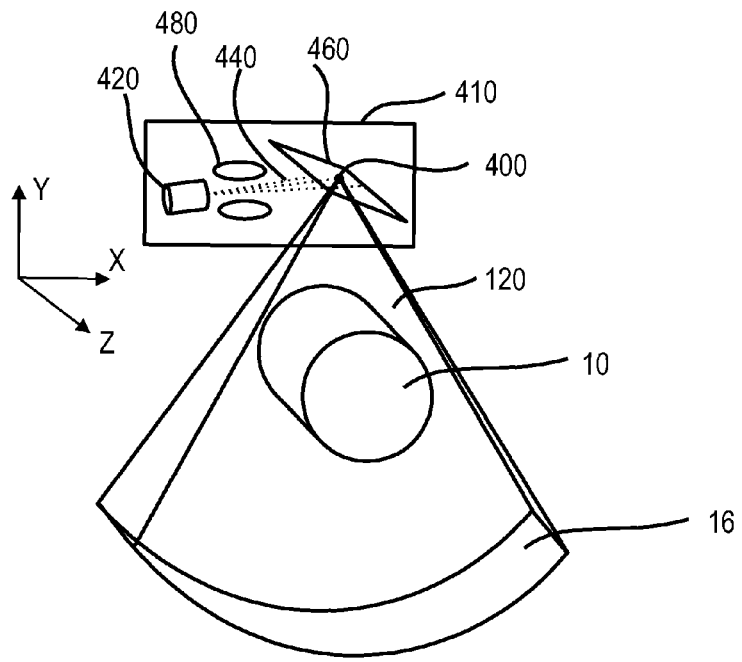
FIG. 8 is a schematic diagram of an x-ray tube that is operative to electronically sweep its focal spot along a defined trajectory in accordance with some embodiments of the present invention.

Reference is now made to FIG. 8 showing a schematic diagram of an x-ray tube that is operative to electronically sweep its focal spot along a defined trajectory in accordance with some embodiments of the present invention. According to some embodiments of the present invention, source trajectories, e.g. source trajectories 300, 320, and 340 are provided by electronically sweeping a focal spot of an x-ray tube rather than by mechanically moving the x-ray tube. Typically, an X ray tube 410 includes a cathode 420 operative to emit a beam of electrons 440 that is accelerated by high voltage toward an anode 460. The electron beam 440 impinges on anode 460 on a focal spot 400 resulting in emission of cone beam 120 through a collimator (not shown). In some exemplary embodiments, movement of the x-ray source e.g. focal spot 400 is provided by magnetically deflecting electron beam 440 with electromagnetic coils 480 so as to alter the position of focal spot 400 on anode 460 in a direction of an axis or rotation of the gantry. Alternatively, electron beam 440 may be deflected by electrostatic grids as known in the art. In some exemplary embodiments, x-ray tube 410 may be similar to x-ray tubes described, for example in incorporated U.S. Pat. No. 5,712,889 and U.S. Pat. No. 7,305,063 or other x-ray tubes that provide for sweeping of the focal spot.

According to some embodiments of the present invention, a collimator associated with the x-ray tube 410 is operative to follow the focal spot position as it is swept along a defined trajectory. According to some embodiments of the present invention, the collimator may be similar to the collimator described herein above.

Figure 9:
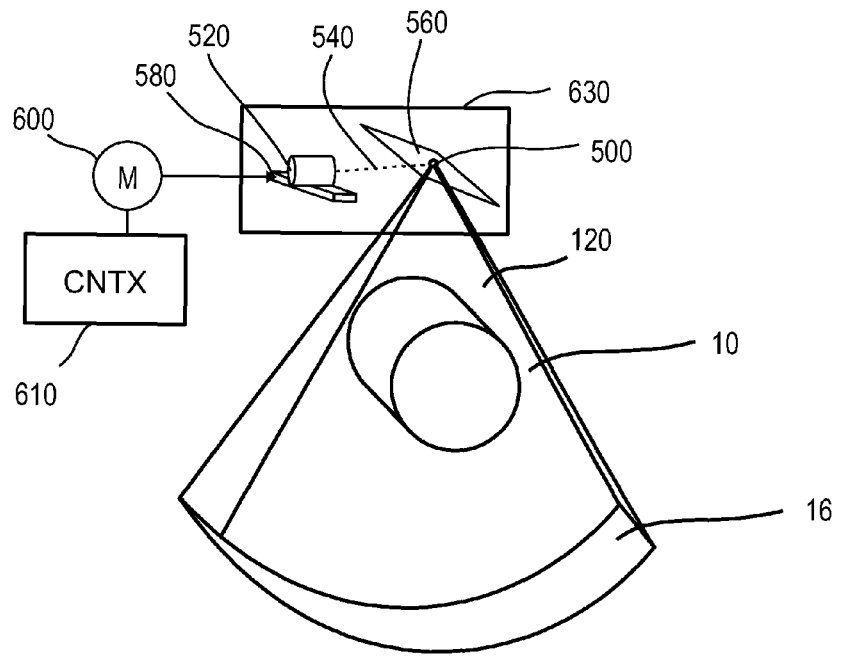
FIG. 9 is a schematic diagram of an x-ray tube that is operative to provide for translation of an x-ray source by translation of its cathode in accordance with some embodiments of the present invention.

Reference is now made to FIG. 9 showing a schematic diagram of an x-ray tube that is operative to provide for translation of an x-ray source by translation of its cathode in accordance with some embodiments of the present invention. According to some embodiments of the present invention, in x-ray tube 630, the motion of the x-ray source is provided by moving a cathode 520 within a vacuum enclosure along a linear rail 580 with a motor 600. As the cathode moves on linear rail 580, a focal spot 500 on an anode 560 is displaced. A controller 610 provides for controlling movement of cathode 520 to obtain a pre-define trajectory of focal spot 500. An advantage in translating cathode 580 as compared to the x-ray tube to obtain a desired trajectory of the focal spot is that the cathode's relatively light weight provides for obtaining motion with improved accuracy and higher speed. According to some embodiments of the present invention, a collimator, as described hereinabove is operative to follow the focal spot position as it moves along its defined trajectory.

Figure 10:
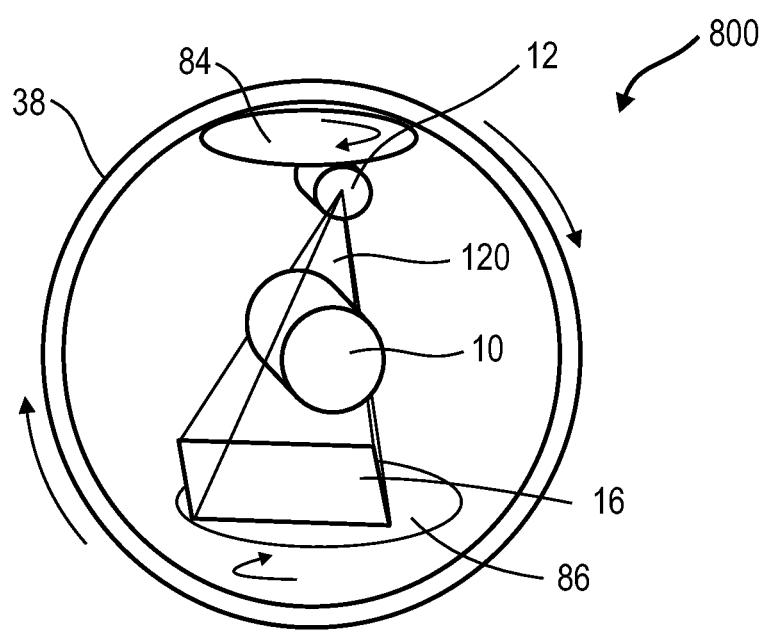
FIG. 10 is a schematic diagram of an x-ray source and detector rotatably mounted on a gantry frame in accordance with some embodiments of the present invention.

Reference is now made to FIG. 10 showing a schematic illustration of an x-ray source and detector rotatably mounted on a gantry frame in accordance with some embodiments of the present invention. According to some embodiments of the present invention, an x-ray source 12 is rotatably mounted on gantry 38 with a rotating member 84. According to some embodiments of the present invention, x-ray source 12 is positioned on rotating member 84 so that it is displaced from its axis of rotation. According to some embodiments of the present invention, rotating member 84 is operable to rotate x-ray source along a circular trajectory in a direction perpendicular to axis of gantry rotation, e.g. Z axis. According to some embodiments of the present invention, a detector 16 is rotatably mounted on gantry 38 with a rotating member 86 and rotation of rotating member 86 is synchronized with rotation of x-ray source 12 so that the line from the focal spot 12 through the center of volume of interest 10 impinge at the center of detector 16. In some exemplary embodiments there is no relative movement between the x-ray source and the detector, they both rotate together about an axis perpendicular to the gantry rotation axis. This configuration is beneficial because it allows fixed collimation relative to the source. It also allows the mounting of anti-scatter grid on the face of the detector such that the anti-scatter grid septa are continuously pointing to the focal spot. In some embodiments, x-ray source 12 and detector 16 are made to keep their orientation respective the gantry rotation axis even though their position is moving about with the rotation of members 84 and 86. These configurations are useful wherein the cone opening angle is wider in the X direction than in the Z direction, as commonly is the case. In such embodiments the X ray beam remains substantially centered at the volume of interest by application of a collimator (not shown) which follows the source motion.

Figure 11A:
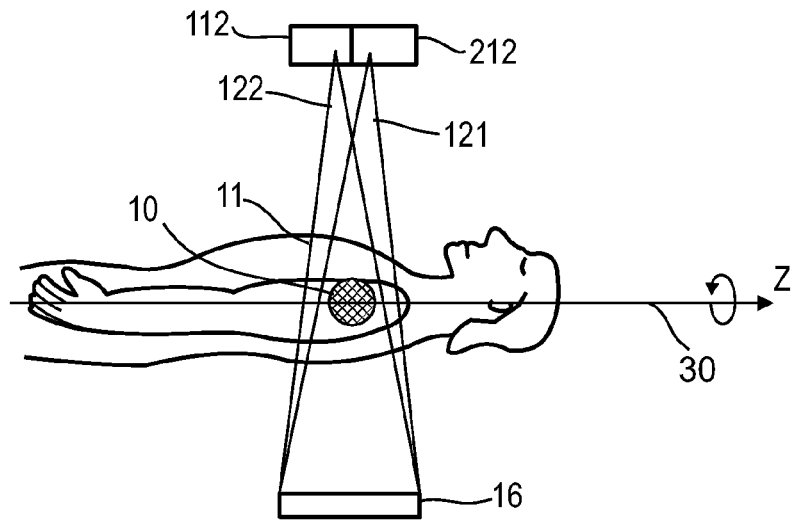
FIGS. 11A-B are schematic diagrams showing multiple cone beam x-ray sources displaced along the Z direction and their respective trajectories over one cycle of gantry rotation in accordance with some embodiments of the present invention.
Figure 11B:
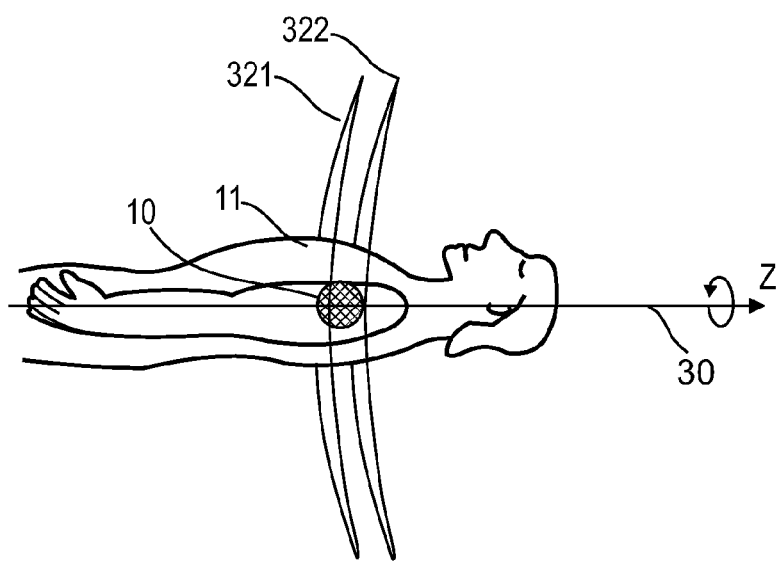

Reference is now made to FIGS. 11A-11B showing multiple cone beam x-ray sources displaced along the Z direction and their respective trajectories over one cycle of gantry rotation in accordance with some embodiments of the present invention. According to some embodiments of the present invention, two sources 112 and 212 displaced along the Z direction partially overlapping beams 121 and 122 which are attenuated by subject 11 and received by detector 16. According to some embodiments of the present invention the multiple sources are activated in sequence so detector 14 receives radiation from one source at any time. In some exemplary embodiments, the switching rate between x-ray sources 112 and 212 is between 500 to 2000 cycles for each rotation of the gantry. Activating the source in sequence provides for using a single detector which saves cost. In some exemplary embodiments overlapping beams 121 and 122 provide for reducing data incompleteness over rotation of the gantry, e.g. partial rotation.

According to some embodiments of the present invention, each of x-ray sources 112 and 212 provide for moving a focal spot of cone beams 121 and 122 (or the x-ray tube) over a pre-defined trajectory. According to some embodiments of the present invention, trajectories similar to trajectories described in reference to FIGS. 7A-7C can be applied to each of x-ray sources 112 and 212. In FIG. 11B, trajectories 321 and 322 are similar to trajectory 320 in FIG. 7B. According to some embodiments of the present invention, motion amplitude for each source in multiple cone beam system (FIG. 11A) is substantially lower than motion amplitude required for a single source system (FIG. 7B).

Persons skilled in the art will appreciate the inventive technique can be applied to dual source or to multiple source CT scanners, wherein the sources are distributed along the Z axis or azimuthally about the rotation axis, and wherein multiple sources may be associated each with a separate detector or be associated with a common detector. Multiple sources may be moved synchronously in the Z direction or may be moved in opposite direction to each other or at other combinations. Any of the configurations described hereinabove for single source CT scanner is applicable for multiple source scanners or for each of a multiplicity of sources separately.

In a fast rotating gantry, the motion in the Z direction of components mounted on the rotating frame may affect the dynamic balancing of the gantry. To overcome this effect, counterweights may be provided for components movable in the Z direction such that movement of system components is counterbalanced by opposite movement of counterweights.

Motion of components along the Z direction is described by a way of example to be facilitated by linear rails and motors. However, other techniques to achieve linear motion or motion on an arc trajectory and are covered by the invention. It is to be understood that any movable component may be provided with an encoder or other means for position measurement and control. Motion of various parts may be synchronized by electronic control circuits or by mechanical gearing or by any other method known in the art.

It is appreciated that although exemplary methods for generating non circular source trajectories by moving the x-ray source in the Z direction while the gantry is rotating has been described, other possible methods generating non circular source trajectories by moving the x-ray source in the Z direction while the gantry is rotating are covered by the invention as well.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A CT scanner comprising:
   at least one cone beam x-ray source assembly mounted on a gantry frame, the gantry frame rotatable about a rotation axis, the x-ray source assembly operable to emit a cone beam at an orientation with respect to the rotation axis;
   a controller operable to translate the at least one source assembly relative to the gantry frame during a rotation cycle in a direction parallel to the rotation axis such that the combined rotation and translation motions form a non-circular continuous source trajectory and to adjust an orientation of the cone beam during a rotation cycle of the gantry while the source is translated relative to the frame, wherein the controller adjusts the orientation to radiate a substantially same volume of interest over the rotation cycle,
   wherein the controller is operable to alter the orientation of the cone beam in a cyclical manner as a function of an angle of rotation of the gantry,
   wherein the controller is operable to alter a position of a focal spot of the x-ray source assembly in synchronization with an adjustment to the orientation,
   wherein movement of the focal spot along the trajectory is cyclical and has a frequency equal to a frequency of rotation of the gantry or an integer multiple of a frequency of rotation of the gantry; and
   a detector array which receives x-rays generated by the at least one cone beam x-ray and produces data signal responsive thereto, said data signals being fed to the controller for the production of a CT image,
   wherein there is no relative motion in the direction of the axis between an object being scanned and the gantry during generation of said data signals.

2. The CT scanner according to claim 1, wherein movement of the focal spot over a cycle of gantry rotation defines an x-ray source trajectory that spans over a plurality of planes perpendicular to the axis of rotation of the gantry.

3. The CT scanner according to claim 1, wherein the controller is operative to move the position of the focal spot linearly in a direction along an axis parallel to the rotational axis of the gantry with respect to the gantry over a cycle of gantry rotation.

4. The CT scanner according to claim 1, wherein the controller is operative to move the position of the focal spot along an arc over a cycle of gantry rotation.

5. The CT scanner according to claim 1, wherein the controller is operative to move the position of the focal spot along a circular trajectory having an axis of rotation perpendicular to the gantry axis of rotation over a cycle of gantry rotation.

6. The CT scanner according to claim 1, wherein the detector array is movably mounted on the gantry and the controller is operative to control movement of the detector array in synchronization with a change in orientation of the cone beam.

7. The CT scanner according to claim 1, comprising a collimator movably mounted on the gantry frame, wherein the collimator is operative to orient the cone beam toward the volume of interest.

8. A CT scanner comprising:
   at least one cone beam X ray source mounted on a gantry frame, the gantry frame rotatable about a rotation axis, the X ray source including a focal spot from which a cone beam is emitted; and
   a controller operable to move a position of the focal spot relative to the gantry frame during rotation of the gantry, wherein the movement relative to the gantry frame is a function of an angle of rotation of the gantry and has a frequency equal to a frequency of rotation of the gantry or an integer multiple of a frequency of rotation of the gantry.

9. The CT scanner according to claim 8 wherein movement of the focal spot relative to the gantry frame over a cycle of gantry rotation and the rotation of the focal spot with gantry rotation defines an x-ray source trajectory that spans over a plurality of planes perpendicular to the axis of rotation.

10. The CT scanner according to claim 9, wherein the x-ray source trajectory is a closed loop trajectory.

11. The CT scanner according to claim 8, wherein the controller is operative to move the position of the focal spot in a direction along an axis parallel to the rotational axis of the gantry.

12. The CT scanner according to claim 8, wherein the controller is operable to adjust an orientation of the cone beam toward a substantially same volume of interest during a rotation cycle of the gantry.

13. The CT scanner according to claim 12, wherein the orientation is defined as function of the position of the focal spot relative to the gantry frame and adjusting the orientation according to the function provides for radiating the substantially same volume of interest as the position of the focal spot changes.

14. The CT scanner according to claim 8, wherein the controller is operative to synchronize detection of the cone beam array with a position of the focal spot.

15. The CT scanner according to claim 14, wherein synchronization provides for cone beam detection over a full extent of translation of the focal spot during a partial scan.

16. The CT scanner according to claim 8 wherein the x-ray source assembly is movably mounted on the gantry frame, and wherein moving the position of the focal spot is provided by moving the position of the x-ray source assembly.

17. The CT scanner according to claim 8, comprising multiple x-ray source assemblies mounted on the gantry frame, wherein at one assembly provides for focal spot translation relative to the gantry frame.

18. The CT scanner according to claim 17, wherein the controller is operable to asynchronously move a focal spot of each assembly during gantry rotation.

19. The CT scanner according to claim 8, wherein the controller is operative to synchronize detection of the cone beam array with a signal from a heart beat monitor.

20. The CT scanner according to claim 8, wherein the controller is operative to move the position of the focal spot linearly in a direction along an axis parallel to the rotational axis of the gantry relative to the gantry over a cycle of gantry rotation.

21. A method for CT scanning, the method comprising:
- aligning a cone beam x-ray source to cover a volume of interest within a region enclosed by a gantry frame, wherein said volume of interest is generally centered about the gantry rotation axis;
- rotating the cone beam source around the volume of interest about a rotation axis;
- moving the cone beam x-ray source along a defined trajectory during said rotation, wherein the trajectory includes a component of translation in the direction of the axis of rotation and wherein the defined trajectory is cyclical and has a frequency equal to a frequency of rotation of the gantry or an integer multiple of a frequency of rotation of the gantry; and
- adjusting orientation of the cone beam x-ray source to consistently point toward the volume of interest over the defined trajectory.

22. The method according to claim 21 wherein the defined trajectory is a function of angular rotation of the gantry.

23. The method according to claim 21, wherein the defined trajectory spans over a plurality of planes.

24. The method according to claim 21, wherein the defined trajectory is a closed loop trajectory over a cycle of gantry rotation.

25. The method according to claim 21, wherein the trajectory includes a circular trajectory parallel to the rotational axis of the gantry.

26. The method according to claim 21 wherein said moving is responsive to a signal from a heart monitor.

27. The method according to claim 21, wherein the movement of the focal spot is linear movement in a direction along an axis parallel to the rotational axis of the gantry with respect to the gantry over a cycle of gantry rotation.

* * * * *